United States Patent
Sugamata

(10) Patent No.: US 7,585,854 B2
(45) Date of Patent: Sep. 8, 2009

(54) METHOD FOR TREATING ENDOMETRIOSIS

(75) Inventor: Masao Sugamata, Nogi-machi (JP)

(73) Assignee: Tochigi Institute of Clinical Pathology, Tochigi (JP)

( * ) Notice: Subject to any disclaimer, the term of this patent is extended or adjusted under 35 U.S.C. 154(b) by 356 days.

(21) Appl. No.: 10/450,954

(22) PCT Filed: Dec. 18, 2001

(86) PCT No.: PCT/JP01/11069

§ 371 (c)(1),
(2), (4) Date: Jun. 18, 2003

(87) PCT Pub. No.: WO02/49670

PCT Pub. Date: Jun. 27, 2002

(65) Prior Publication Data

US 2004/0024016 A1    Feb. 5, 2004

(30) Foreign Application Priority Data

Dec. 18, 2000   (JP)   ............................. 2000-383224

(51) Int. Cl.
*A61K 31/553* (2006.01)
*A61K 31/44* (2006.01)
*A01N 43/16* (2006.01)

(52) U.S. Cl. .................. 514/211.09; 514/279; 514/453

(58) Field of Classification Search ............ 514/211.09, 514/279, 453
See application file for complete search history.

(56) References Cited

FOREIGN PATENT DOCUMENTS

WO    WO 99/32125    7/1999

OTHER PUBLICATIONS

Ono Pharmaceutical (2000) Company News.*
Rees, M.C.P. et al. (1987) Leukotriene release by endometrium and myometrium throughout the menstrual cycle in dysmenorrhoea and menorrhagia. J Endocr. 113, 291-295.*
Jafaru, I. Abu et al., Human Reproduction Update, May-Apr. 2000, vol. 6, No. 2, pp. 200-206.
Numao, Toshio, Igaku No Ayumi, (1997), vol. 180, No. 1, pp. 70-74.
Uchide, Ichiro. Nippon Sanka Fujinka Gakkai Zasshi, (2001), vol. 53, No. 2, p. 510.
Uchide, Ichiro. Nippon Funin Gakkai Zasshi, Oct. 1, 2000, vol. 45, No. 4, p. 268.
Liang et al., Journal of Guangzhou University of Traditional Chinese Medicine, vol. 16, No. 4, pp. 283-284 (Dec. 1999).

* cited by examiner

*Primary Examiner*—Sreeni Padmanabhan
*Assistant Examiner*—Renee Claytor
(74) *Attorney, Agent, or Firm*—Birch, Stewart, Kolasch & Birch, LLP

(57) ABSTRACT

A drug effective for prevention and therapy of endometriosis is disclosed. The drug for prevention and/or therapy of endometriosis according to the present invention comprises an antiallergic agent as an effective ingredient.

10 Claims, No Drawings

METHOD FOR TREATING ENDOMETRIOSIS

This application is the national phase under 35 U.S.C. § 371 of PCT International Application No. PCT/JP01/11069 which has an International filing date of Dec. 18, 2001, which designated the United States of America.

TECHNICAL FIELD

The present invention relates to a drug for prevention and/or therapy of edometriosis

BACKGROUND ART

Endometriosis is a disease wherein endometrium or endometrium-like tissue ectopically proliferates at a site other than the inner surface of the cavity of uterus which is the natural site thereof. The cause of endometriosis is unknown, and therapies such as separation of the adhered tissues by surgery, administration of hormones and administration of analgesics are performed. However, these therapies are symptomatic treatments, and no complete therapy exists.

DISCLOSURE OF THE INVENTION

An object of the present invention is to provide a drug effective for prevention and therapy of endometriosis.

The present inventor studied by staining ectopical endometrium-like tissue (endometriosis sample) and the tissue sampled from the same site of the healthy individuals by various staining methods, and observing them with an light microscope and an electron microscope. As a result, in the endometriosis samples from patients suffering from endometriosis, invasion of mast cells and degranulation thereof, as well as proliferation of interstitial component were observed. These are the typical symptoms of type I allergy, so that it was found that the essence of endometriosis is an allergic inflammation. The present inventor thought that it might be possible to cure endometriosis by an antiallergic agent, and administered a plurality of commercially available antiallergic agents to endometriosis animal model to examine their therapeutic effects. As a result, as expected, it was experimentally confirmed that the symptoms of endometriosis are clearly inhibited by the antiallergic agents, thereby completing the present invention.

That is, the present invention provides a drug for prevention and/or therapy of endometriosis comprising an antiallergic agent as an effective ingredient. The present invention also provides a use of an antiallergic agent for the production of a drug for prevention and/or therapy of endometriosis. The present invention further provides a method for prevention and/or therapy of endometriosis comprising administering an antiallergic agent to a patient suffering from endometriosis, in an amount effective for the prevention or therapy of endometriosis.

By the present invention, a drug effective for prevention and therapy of endometriosis, which can cure endometriosis was first provided. The number of patients suffering from endometriosis is now rapidly increasing, and endometriosis is now one of the main causes of menorrhalgia and infertility. Thus, the present invention is thought to greatly contribute in the field of therapy of infertility, and therapy and prevention of menorrhalgia.

BEST MODE FOR CARRYING OUT THE INVENTION

As mentioned above, the drug for prevention or therapy of endometriosis according to the present invention is effective for both prevention and therapy of endometriosis (that is, the drug may be used as a drug for therapy, as a drug for prevention, and as a drug simultaneously aiming at therapy and prevention), and comprises an antiallergic agent as an effective ingredient.

The present inventor first discovered in the world that the essence of endometriosis is an allergic inflammation. The present invention was made based on this discovery. Since the symptoms of the endometriosis can be lightened by lightening the symptoms of the allergy, any antiallergic agents effective for therapy and/or prevention of allergies may be employed as the antiallergic agent contained as the effective ingredient in the drug for prevention and/or therapy of endometriosis according to the present invention.

The antiallergic agent used in the present invention is an inhibitor or an antagonist against the type I allergy reaction, and includes inhibitors for release of chemical mediators from mast cells, synthetase inhibitors and chemical mediator antagonists (such as antihistamic agents). Various such antiallergic agents are known and used for the therapies of bronchial asthma, allergic rhinitis and allergic dermatitis which are representative diseases of type I allergy, and both those having antihistaminic action and not having antihistaminic action are included. Examples of the antiallergic agent which may be used in the present invention include cromoglycic acid, tranilast, amlexanox, repirinast, tazanolast, pemirolast K, suplatast, ketotifen, azelastine, oxatomide, terfenadine, mequitazine, emedastine, epinastine, astemizole, ibudilast, ozagrel, seratrodast, pranlukast, ebastine, cetirizine, cyproheptadine, chlorophenylamine, homochiorcyclizine, hydroxyzine and clemastine, as well as pharmaceutically acceptable salts and hydrates thereof. Among these, epinastine, ketotifen and pranlukast, as well as pharmaceutically acceptable salts and hydrates thereof are especially preferred.

Examples of the pharmaceutically acceptable salts include acid addition salts such as hydrochloric acid salt, sulfuric acid salt, fumaric acid salt, maleic acid salt, tartaric acid salt, citric acid salt and tosylic acid salt, as well as metal salts such as sodium salt, potassium salt and calcium salts when the active compound is an acid, although the pharmaceutically acceptable salts are not restricted thereto.

The drug for prevention and/or therapy of endometriosis according to the present invention may be administered through the route permitted to the antiallergic agent contained as the effective ingredient. Administration routes include oral administration, and parenteral administration routes such as intravenous, subcutaneous, intramuscular and rectal administration. Usually, oral administration is preferred because it is simple. Although the administration dose is appropriately selected depending on the degree of the symptom of the patient, type of the antiallergic agent and the like, the dose is, for example, about 10 to 20 mg in the case of epinastine hydrochloride per day per adult. The antiallergic agents are effective at the administration doses employed for the therapy of allergies by the respective antiallergic agent.

Adenomyosis of uterus is the state that the endometrium or endometrium-like tissue ectopically proliferates in myometrium, so that it is a form of endometriosis and is included in endometriosis ("Surgical Pathology", p.713-715, published by Bunkodo; "Clinical Histopathology", p.661, published by Kyorin Shoin).

As for the formulation of the drug, any formulation methods ordinarily employed in the field of pharmaceuticals may be employed. For example, the antiallergic agent may be granulated together with an additive such as lactose, a polyoxyethylenesorbitan fatty acid ester, propylene glycol or sodium laurate, and the resultant may be made into tablets, but the formulation method is not restricted thereto. The above-mentioned various antiallergic agents are commercially available in formulated forms, these formulated antiallergic agents may be employed in the present invention.

Since antiallergic agents have already been used as therapeutic agents for various allergies such as bronchial asthma, allergic rhinitis and allergic dermatitis, safeties thereof to the extent demanded for pharmaceuticals have been confirmed.

The present invention will now be described more concretely by way of examples. However, the present invention is not limited to the following examples.

REFERENCE EXAMPLE 1

Observation of Human Endometriosis Specimens

Adhered lesions in pelvic cavity were sampled from patients suffering from endometriosis (external endometriosis), and stained by hematoxylin-eosin staining or toluidine blue staining according to the conventional methods, followed by observation of the stained samples with an light microscope. The magnification was 10× when observing the hematoxylin-eosin-stained specimens, and 20× or 100× when observing the toluidine blue-stained specimens. The tissue was also subjected to uranium-lead double staining according to the conventional method, and the obtained specimens were observed with an electron microscope at a magnification of 3000× to 5000×.

As a result, in the toluidine blue-stained specimens of the tissues from patients suffering from endometriosis, invasion of mast cells was observed. Further, by the observation with the electron microscope, degranulation of mast cells was observed in addition to the invasion of the mast cells. Still further, collagen fibers which are the main result of the growth of the interstitial component. On the other hand, in the specimens from healthy individuals, invasion and degranulation of mast cells, and collagen fibers were not observed. Invasion of mast cells and their degranulation are the symptoms of type I allergy. From the above-described observations with microscopes, it was discovered that the essence of endometriosis is an allergic inflammation.

COMPARATIVE EXAMPLE 1

Observation of Non-Treated Endometriosis Model Rats

Endometriosis model rats were prepared by the method described in Michael W. Vernon et al., FERTILITY AND STERILITY, Vol. 44, No. 5, November 1985. That is, endometriosis model rats were prepared as follows: Sprague-Dawley rats (female) of 8 weeks old were acclimatized for 2 weeks under 12 hours light-dark condition. From each rat, right uterine horn was excised under general anesthesia with sevoflurane and ketamine hydrochloride, and a tissue piece sizing 5 mm×5 mm was prepared therefrom. The tissue piece was subjected to autotransplantation such that the endometrium surface is attached to peritoneum.

Seven days after the preparation of the model rats, at which the model lesion reached its peak, the peritoneum tissue including the graft up to the abdominal muscle was excised to obtain a lesion sample. From the thus obtained samples, light microscope specimens (hematoxylin-eosin staining, toluidine blue staining) and electron microscope specimens (uranium-lead double staining) were prepared, and observations with an light microscope (the magnifications were 4× for hematoxylineosin-stained specimens, and 20× for toluidine blue-stained specimens, respectively), and with an electron microscope were carried out as in Reference Example 1.

As a result, invasion of mast cells and proliferation of interstitial cells were observed by the toluidine blue staining, and invasion of eosinophils and lymphocytes was observed by the observation with the electron microscope.

EXAMPLE 1

Therapeutic Effect by Administration of Epinastine Hydrochloride

Endometriosis model rats were prepared by the same method as in Comparative Example 1. From 24 hours after the preparation of the endometriosis model rats, an antiallergic agent (trademark "Alesion Tablet" produced by Boehringer Ingelheim) containing epinastine hydrochloride as the active component was orally administered to the rats for 6 days at a dose of 0.04 mg/kg bodyweight per day in terms of epinastine hydrochloride. Seven days after the preparation of the model rats, at which the model lesion reached its peak, the peritoneum tissues including the graft up to the abdominal muscle were excised to obtain lesion samples. The obtained pathological samples were stained as in Reference Example 1, and the resultants were observed with an light microscope and with an electron microscope.

As a result, the invasion of mast cells was apparently reduced when compared with the case of Comparative Example 1. By the observations with the light microscope and with the electron microscope, apoptosis of fibroblast cells was observed, and prominent inhibition of proliferation of the interstitial cells by the induction of apoptosis of interstitial cells, especially fibroblast cells was observed. From these, it was proved that epinastine is effective for the therapy of endometriosis.

EXAMPLE 2

Therapeutic Effect by Administration of Ketotifen Fumarate

The same procedures as in Example 1 were repeated except that an antiallergic agent containing ketotifen fumarate as the active component (trademark "Zaditen" produced by Ciba-Geigy Japan Limited) was administered in place of the antiallergic agent containing epinastine hydrochloride as an active component.

As a result, the invasion of mast cells was apparently reduced when compared with the case of Comparative Example 1. By the observations with the light microscope and with the electron microscope, apoptosis of fibroblast cells was observed, and prominent inhibition of proliferation of the interstitial cells by the induction of apoptosis of interstitial cells, especially fibroblast cells was observed. From these, it was proved that ketofetin is effective for the therapy of endometriosis.

EXAMPLE 3

Therapeutic Effect by Administration of Pranlukast Hydrate

The same procedures as in Example 1 were repeated except that an antiallergic agent containing pranlukast hydrate as the active component (trademark "ONON CAPSULE" produced by ONO PHARMACEUTICAL CO.,LTD.) was administered in place of the antiallergic agent containing epinastine hydrochloride as an active component, and that the administration dose per day was 9 mg/kg in terms of pranlukast hydrate.

As a result, the invasion of mast cells was prominently reduced when compared with the case of Comparative Example 1. The effect for inhibiting invasion of mast cells was more prominent than in Examples 1 and 2. By the observations with the light microscope and with the electron microscope, apoptosis of fibroblast cells was observed, and prominent inhibition of proliferation of the interstitial cells by the induction of apoptosis of interstitial cells, especially fibroblast cells was observed. From these, it was proved that pranlukast is effective for the therapy of endometriosis.

The invention claimed is:

1. A method for therapy of endometriosis comprising administering an antiallergic agent to a patient suffering from endometriosis, in an amount effective for the therapy of endometriosis wherein said antiallergic agent is epinastine or pharmaceutically acceptable salts thereof, ketotifen or pharmaceutically acceptable salts thereof or pranlukast or pharmaceutically acceptable salts or hydrates thereof.

2. The method according to claim 1, wherein said antiallergic agent is administered orally or parenterally.

3. The method according to claim 1, wherein said pharmaceutically acceptable salts are acid addition salts or metal salts.

4. The method according to claim 1, wherein said antiallergic agent is administered orally.

5. The method according to claim 1, wherein said antiallergic agent is epinastine or ketotifen, or pharmaceutically acceptable salts thereof.

6. A method for therapy of endometriosis, comprising:
administering an antiallergic agent to a patient suffering from endometriosis, in an amount effective for the therapy of endometriosis, wherein endometriosis is defined as an allergic inflammation and is a type I allergy wherein said antiallergic agent is epinastine or pharmaceutically acceptable salts thereof, ketotifen or pharmaceutically acceptable salts thereof or pranlukast or pharmaceutically acceptable salts or hydrates thereof.

7. The method according to claim 6, wherein said pharmaceutically acceptable salts are acid addition salts or metal salts.

8. The method according to claim 6, wherein said antiallergic agent is administered orally.

9. The method according to claim 6, wherein said antiallergic agent is pranlukast, or pharmaceutically acceptable salts or hydrates thereof.

10. A method for therapy of endometriosis, comprising:
administering an antiallergic agent to a patient suffering from endometriosis in an amount effective for the therapy of endometriosis, wherein endometriosis is defined as an allergic inflammation and is a type I allergy or adenomyosis wherein said antiallergic agent is epinastine or pharmaceutically acceptable salts thereof, ketotifen or pharmaceutically acceptable salts thereof or pranlukast or pharmaceutically acceptable salts or hydrates thereof.

* * * * *

UNITED STATES PATENT AND TRADEMARK OFFICE
CERTIFICATE OF CORRECTION

| | |
|---|---|
| PATENT NO. | : 7,585,854 B2 |
| APPLICATION NO. | : 10/450954 |
| DATED | : September 8, 2009 |
| INVENTOR(S) | : Masao Sugamata |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 735 days.

Signed and Sealed this

Fourteenth Day of September, 2010

David J. Kappos
*Director of the United States Patent and Trademark Office*